US006019977A

United States Patent [19]

Joseph

[11] Patent Number: 6,019,977

[45] Date of Patent: Feb. 1, 2000

[54] PROCESSING FOR PREVENTING PRECIPITATES IN FRESH PRESSED ECHINACEA JUICES

[75] Inventor: Heinz Walter Joseph, Berg, Germany

[73] Assignee: Plantamed Arzneimittel GmbH, Germany

[21] Appl. No.: 09/136,670

[22] Filed: Aug. 19, 1998

[30] Foreign Application Priority Data

Aug. 20, 1997 [EP] European Pat. Off. .............. 97114376

[51] Int. Cl.[7] ...................................................... A01N 65/00

[52] U.S. Cl. .......................................................... 424/195.1

[58] Field of Search .......................... 424/195.1; 426/590

[56] References Cited

U.S. PATENT DOCUMENTS 3,035,975 5/1962 Voigt .................................... 424/195.1

FOREIGN PATENT DOCUMENTS 2721014 11/1978 Germany .
2721014 10/1987 Germany .
4438589 10/1994 Germany .................................. 35/78
4438589 3/1995 Germany .

*Primary Examiner*—Thurman K. Page
*Assistant Examiner*—Todd D Ware
*Attorney, Agent, or Firm*—Ladas & Parry

[57] ABSTRACT

A process for preventing precipitates in fresh pressed echinacea plant juice comprising cooling the fresh pressed plant juice obtained for a short time, followed by filtration and stabilisation by the addition of acid. The pressed plant juice is preferably cooled to temperatures between 0 and −15° C. for less than 14 days and after filtration adjusted to a pH value below 6 by adding 0.01 to 5% of a polyvalent carboxylic acid, preferably citric acid.

7 Claims, No Drawings

PROCESSING FOR PREVENTING PRECIPITATES IN FRESH PRESSED ECHINACEA JUICES

The present application relates to a process for preventing precipitates in fresh pressed juices of echinacea. In addition, the application relates to stabilised pressed echinacea juices and drug forms containing the same.

Echinacea preparations are used internally as urological medicaments, influenza remedies, antiphlogistics and stimulants. Externally they used for treating wounds.

Echinacea preparations, especially in the form of tinctures and pressed juices, have been in use for a long time and are a well-known natural remedy. The tendency of pressed plant juices to form precipitates has been known for as long as their use. To overcome this problem, the pressed juice is usually left standing for a very long period of time, generally about two years, and the precipitates formed during that period then filtered off to obtain a clear pressed plant juice.

Despite said first precipitation during the two-year storage period, however, these clear filtrates tend to form precipitates and flocculates after being filled in bottles for sale which results in negative patient compliance. In addition, there is the possibility that the precipitates formed clog or narrow the droppers thus preventing exact dosing. Both manifestations often result in the preparation being returned to the manufacturer as being decayed or unfit for use.

In addition, manufacturers are faced with cost and storage problems due to the long storage time required for the fresh pressed juices before they can be filled into dosage units for sale to the consumers.

It is the object of the present invention to provide a process that prevents such precipitates and permits earlier bottling of the pressed juice into dosage units for sale to the consumer, thus solving both the problem of unsatisfactory patient compliance and the problem of long storage times.

Surprisingly, we have now found that the excessive storage time of two years can be avoided by cooling the fresh pressed plant juice to temperatures below 0° C. for a short time, filtering the solution and stabilising said solution by the addition of acid. This approach results in a significant stabilisation of the fresh pressed plant juice obtained so that even after several months no clouding or precipitation will occur.

In addition, the process of the invention overcomes the necessity of storing the pressed plant juice for a long time, practically waiting for the first precipitation. Rather, the pressed juices may be processed immediately, do not take up storage capacity and are much more stable than conventional preparations.

In accordance with the invention, the fresh pressed juice is stored in a cool place for a short period of 14 days or less, preferably 1 to 5 days and even more preferably 2 to 3 days. The storage temperature for purposes of the invention is between 0 and −15° C., preferably −5 to −10° C. and most preferably −8° C.

After such cool storage the pressed plant juice is filtered until clear. Said filtration can be carried out by means of conventional processes usually used for pressed plant juices, e.g. by means of sieve or paper filters, cellulose filters, membranes or by centrifugation and other processes suitable for separating solids from solutions.

After filtration of the cooled pressed plant juice, the pH is adjusted to a value below 6.0 by the addition of acid. Preferably the adjusted pH value is in the range of 4.5 to 5.3 and even more preferably in the range of 4.9 to 5.0.

The acid used for adjusting the pH is a carboxylic acid found in nature, preferably a polyvalent carboxylic acid, which must be physiologically compatible. Such acids comprise but are not limited to tartaric acid, amino acids found in nature and the acids of the citrate cycle, especially citric acid, malic acid, fumaric acid, itaconic acid, aconitic acid, succinic acid, lactic acid, glutamic acid, asparaginic acid, oxalic acid and ascorbic acid. Malic acid, fumaric acid and citric acid are particularly preferred, the latter being most preferred.

The acid is added in an amount required for adjusting the pH. This amount depends on the strength of the acid and the original pH of the preparation to be adjusted. As a rule, 0.01 to 5% of acid, preferably 0.05 to 1% of acid and most preferably 0.1% (w/v) of acid are used.

The above-mentioned pressed plant juice may be present in the form of tinctures, fluid extracts and pressed plant juices as well as preparations containing the same. Preferably it is an ethanolic pressed juice preparation containing 20 to 60% of pressed echinacea juice and even more preferably an ethanolic preparation containing 80% of pressed echinacea juice.

EXAMPLE

For the purpose of stabilisation, a pressed echinacea plant juice stabilised to a final ethanol content of 20% was cooled to −8° C. for three days and then filtered through a cellulose filter for clarification. The clear solution thus obtained was adjusted to a pH of 4.9 by the addition of 0.1% of citric acid.

The finished solution was filled into bottles and stored at room temperature for observation. The product thus obtained turned out to be stable for a long time (more than 24 months); no precipitates were observed.

In comparison, a pressed plant juice stored for a period of two years according to the conventional process was filtered until clear and filled into bottles. After only two months, this preparation had become visibly cloudy and was thus less attractive for the user.

I claim:

1. A process for preventing precipitates in pressed Echinacea plant juices consisting essentially of cooling the fresh pressed plant juices for 14 days or less to temperatures between 0 and −15° C., subsequent filtration of the solution until clear and adjusting said solution to a pH value between 4.5 and 6 with a carboxylic acid selected from the group consisting of citric acid, tartaric acid, malic acid, fumaric acid, itaconic acid, aconitic acid, succinic acid, glutamic acid, asparaginic acid, oxalic acid and ascorbic acid.

2. A process according to claim 1 wherein the acid is citric acid.

3. A process according to claim 2 wherein the acid is added in an amount of 0.01 to 5% (w/v).

4. A process according to claim 3 wherein the pressed Echinacea plant juice is cooled to −8° C. for two to three days, subsequently filtered and then adjusted to a pH value of 4.9 by adding 0.1% of citric acid.

5. A stabilized Echinacea plant juice produced according to the process of any one of claims 1 to 4.

6. The stabilized pressed plant juice according to claim 5 comprising 0.1% of citric acid.

7. A drug composition comprising a pressed plant juice according to claim 6.

* * * * *